United States Patent [19]
Avramenko et al.

[11] Patent Number: 6,013,075
[45] Date of Patent: Jan. 11, 2000

[54] MEDICAL COAGULATION APPARATUS

[75] Inventors: Stanislav Avramenko; Igor Stoupine, both of Tokyo, Japan

[73] Assignee: Technova Incorporated, Tokyo, Japan

[21] Appl. No.: 08/860,547

[22] PCT Filed: Dec. 27, 1995

[86] PCT No.: PCT/JP95/02720

§ 371 Date: Sep. 12, 1997

§ 102(e) Date: Sep. 12, 1997

[87] PCT Pub. No.: WO96/20653

PCT Pub. Date: Jul. 11, 1996

[30]     Foreign Application Priority Data

Dec. 30, 1994 [JP] Japan .................................. 6-339371

[51] Int. Cl.[7] .................................................. A61B 17/39
[52] U.S. Cl. ................................ 606/40; 606/42; 606/49; 219/121.48; 219/121.54
[58] Field of Search ................................. 606/40, 42, 49; 219/121.39, 121.48, 121.54

[56]                  References Cited

U.S. PATENT DOCUMENTS 4,839,492  6/1989  Bouchier et al. .
4,901,719  2/1990  Trenconsky et al. .
5,088,997  2/1992  Delahuerga et al. .

FOREIGN PATENT DOCUMENTS 62-240043  10/1987  Japan .
63-215374   9/1988  Japan .
 4-220248   8/1992  Japan .

*Primary Examiner*—Lee Cohen
*Attorney, Agent, or Firm*—Finnegan, Henderson, Farabow, Garrett & Dunner, L.L.P.

[57]                ABSTRACT

Medical coagulation apparatus which reduces current that flows through the interior of a living body, and which does not produce thermal burning accidents caused by high-frequency current in an opposing electrode. Current generated by resonance on a secondary side L2 of a monostable multivibrator M flows into a primary side L1 from an amplifier 39. As a result, a high potential is generated on the secondary side L2 so that a unipolar discharge is produced by a needle electrode 16 connected to the secondary side. An arc discharge at the needle electrode 16 is guided by argon gas jetted from a nozzle 14 of a hand piece 10, irradiates tissue of a living body 50 and coagulates the tissue. The medical coagulation apparatus does not require an opposing electrode plate because the needle electrode 16 connected to the secondary side of the transformer produces the unipolar discharge.

8 Claims, 7 Drawing Sheets

6,013,075

MEDICAL COAGULATION APPARATUS

TECHNICAL FIELD

This invention relates to a medical coagulation apparatus and, more particularly, to a surgical coagulation apparatus for irradiating living tissue with an electric discharge to achieve coagulation and hemostasis.

BACKGROUND ART

Electric scalpels are employed widely as surgical devices. An electric scalpel is an instrument which, by passing a high-frequency current of from several hundred kilohertz to several megahertz at a power of several hundred watts into an electrode at the slender scalpel tip of its distal end, is used instead of a knife to make an incision and coagulate tissue. When the electric scalpel is employed for the coagulation and hemostasis of tissue, the high-frequency current is passed into the tissue, which has been contacted by the scalpel tip electrode, in concentrated fashion at a single point, whereby the protein in the tissue is coagulated and desiccated by Joule heating produced in the tissue.

Since the scalpel tip electrode is contacted with the tissue when the electric scalpel is used for coagulation and hemostasis, the coagulated tissue tends to adhere to the scalpel tip electrode and peel off, as a result of which the tissue is damaged. An electric scalpel having a spray coagulation function is available as an electric scalpel that is capable of achieving non-contact coagulation and hemostasis. By applying a high voltage (on the order of twice that applied in the ordinary electric scalpel) to electrodes, this electric scalpel coagulates tissue by irradiating the tissue with an arc discharge under conditions in which the electrodes are held several millimeters away from the tissue in air. However, since the discharge is effected in highly insulative air, control of the arc discharge is difficult, more current flows than is necessary and excessive coagulation and tissue carbonization readily occur. An argon beam coagulator has been proposed in Japanese Patent Laid-Open Publication No. 62-240043 in order to solve this problem. According to this art, an opposing electrode plate 80 is affixed to a living body 50, as shown in FIG. 6, and the living body 50 is held at the same potential as that of the opposing electrode plate 80. A pencil-shaped device 110 is then supplied with argon gas from a gas supply unit 120 and an electrode 116 provided on the pencil-shaped device 110 is supplied with high-frequency current from a control unit 130. As a result, an arc discharge is produced from the electrode 116 to the living body 50 held at the same potential as that of the opposing electrode plate 80 and argon gas ionized by the arc discharge is jetted toward the body so that a high-frequency current is introduced into the tissue in non-contacting fashion as an arc discharge in argon gas, whereby coagulation and hemostasis of the tissue are achieved. Since the ionized argon gas possesses conductivity, this method is such that a stable arc beam can be emanated toward the tissue so that uniform coagulation is possible with little energy.

DISCLOSURE OF THE INVENTION

However, the above-described argon beam coagulator and, in similar fashion, the electric scalpel and spray coagulating-type electric scalpel, employ an arrangement in which current from the electrode 116 is introduced to the opposing electrode plate 80 via the living body, as illustrated in FIG. 6. As a consequence, the patient often sustains thermal burns when the devices are used, and this has a serious effect upon patients who are in a seriously weakened state after surgery. Accordingly, it is required that thermal burning be dealt with rapidly. Thermal burning mainly occurs at the location where the opposing electrode is affixed. More specifically, a generally employed opposing electrode has an area of 100~200 cm$^2$. However, in situations where the area of contact is small or contact unsatisfactory, current flows into a portion of the opposing plate in concentrated fashion and thermal burning occurs at this portion. Further, attaching the opposing electrode to the patient at the time of surgery is a troublesome operation and it is very difficult to attach the opposing electrode securely to a patient for whom repose is required. In addition, thermal burning occurs at the cord. Specifically, since high-voltage, high-frequency power is fed to the scalpel tip electrode via a cord, the sheath of the scalpel tip electrode cord can come off, exposing the inner wire which may then contact the patient. In a case where the scalpel tip electrode cord lies underneath the body, a high-frequency current flows owing to inductive coupling, thereby causing thermal burning. Further, since current flows within the living body situated between the discharge unit and the opposing electrode plate, there is the danger that the living body will be adversely affected.

The present invention has been devised to solve the foregoing problems and an object thereof is to provide a medical coagulation apparatus for reducing the current that flows through a living body, the apparatus being free of thermal burning accidents caused by high-frequency current at an opposing electrode plate.

In order to attain the foregoing object, a medical coagulation apparatus is characterized by comprising inert gas supply means for supplying an inert gas, a casing formed to have a size capable of being grasped and having a jet nozzle for guiding the inert gas supplied from the inert gas supply means, a transformer housed within the casing and having a winding of a small number of turns wound on a primary side and a winding of a large number of turns wound on a secondary side, one end of the secondary side floating or being connected to the primary side and the other end being connected to a discharge portion placed in the proximity of the jet nozzle of the casing, and power supply means connected to the primary side of the transformer for producing a single-pole discharge at the discharge portion connected to the secondary side of the transformer, accumulating electric charge on the surface of a living body by electrostatic induction between the apparatus and the living body, and passing a current, which has a frequency that generates a high potential for supplying electrical energy, into the primary side.

In a preferred embodiment of the above medical coagulation apparatus, the power supply means passes a current, which has a frequency that causes resonance on the secondary side of the transformer, into the primary side.

In order to attain the foregoing object, a further medical coagulation apparatus is characterized by comprising inert gas supply means for supplying an inert gas, a casing formed to have a size capable of being grasped and having a jet nozzle for guiding the inert gas supplied from the inert gas supply means, a transformer housed within the casing and having a winding of a small number of turns wound on a primary side and a winding of a large number of turns wound on a secondary side, one end of the primary side floating, one end of the second side floating or being connected to the primary side and the other end being connected to a discharge portion placed in the proximity of the jet nozzle of the casing, power supply means connected to the other end of the primary side of the transformer for passing a current of a regulated frequency into the primary side, and frequency regulating means for producing a single-pole discharge in the discharge portion connected to the secondary side of the transformer, accumulating electric charge on the surface of a living body by electrostatic induction between the apparatus and the living body, and regulating frequency of the power supply means to a frequency that generates a high potential for supplying electrical energy.

In a preferred embodiment of the above medical coagulation apparatus, the frequency regulating means regulates the frequency of the power supply means to a frequency that causes resonance on the secondary side of the transformer.

BEST MODES FOR CARRYING OUT THE INVENTION

Embodiments which specify the present invention will now be described with reference to the drawings.

Figure 1:
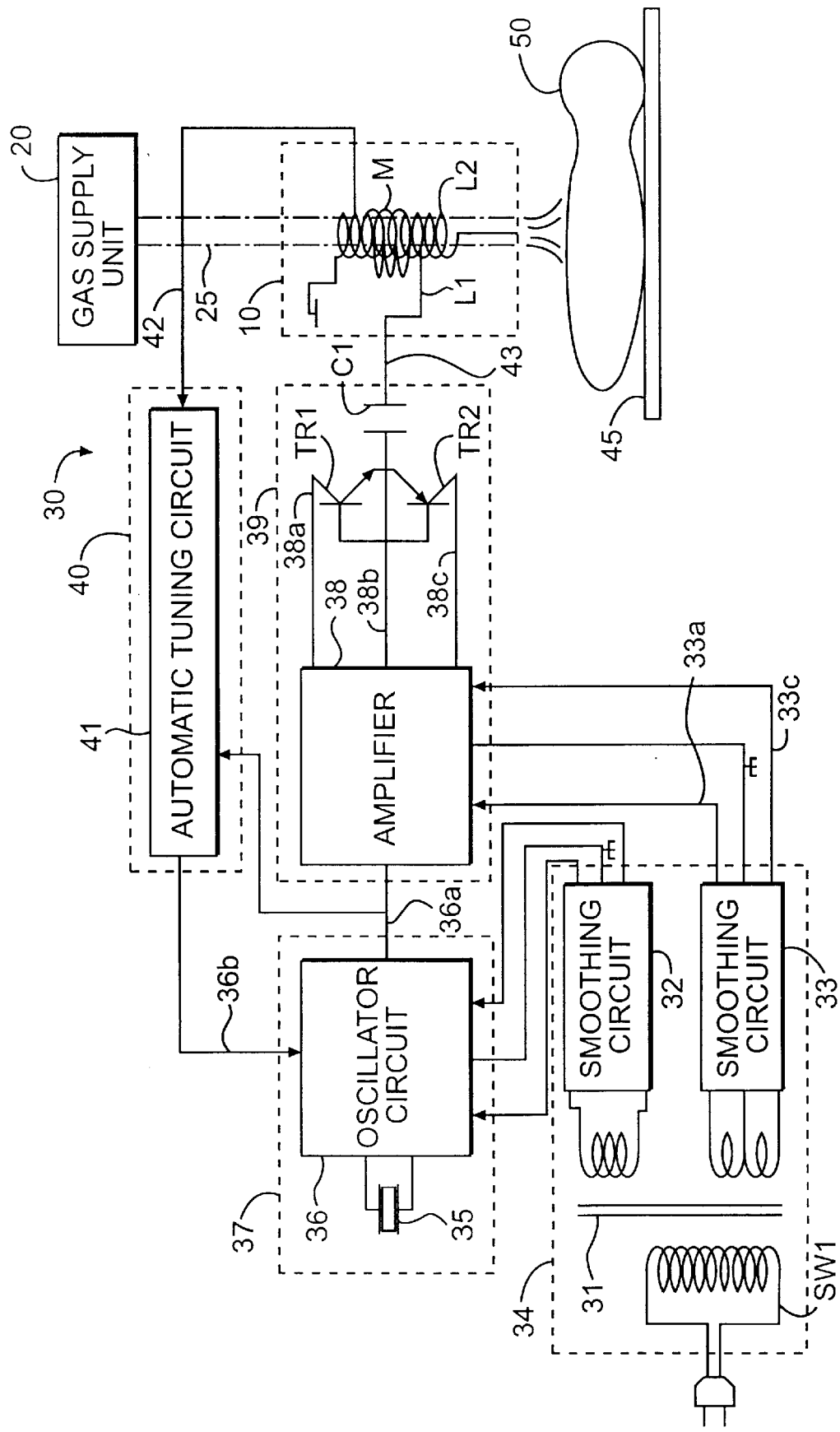
FIG. 1 is a block diagram illustrating the construction of a medical coagulation apparatus according to a first embodiment of the present invention.

FIG. 1 shows the construction of a medical coagulation apparatus according to a first embodiment of the present invention. The medical coagulation apparatus comprises a hand piece 10 for effecting coagulation and hemostasis of an affected part by irradiating a living body 50, which lies on an insulated operating table 45, with an arc discharge while a gas stream is jetted from a nozzle, a power supply unit 30 for supplying the hand piece 10 with electric power, and a gas supply unit 20 for supplying the hand piece 10 with an inert gas.

The power supply unit 30 consists of a power supply section 34 comprising a transformer 31 for boosting a commercial power supply, a first smoothing circuit 32 for smoothing the boosted voltage and a second smoothing circuit 33, an oscillator section 37 comprising an oscillator circuit 36 having a crystal oscillator 35, an amplifier section 39 comprising an amplifier 38, a first transistor TR1, a second transistor TR2 and a tuning capacitor C1, and a tuning section comprising an automatic tuning circuit 41 for tuning the oscillating frequency of the oscillator section 37 to the resonance frequency of a monostable multivibrator M, described later. The output of the power supply unit 30 is fed to the hand piece 10 from the amplifier section 39 via a line 43, and the gas supply unit 20 consists of a gas tank (not shown) storing argon, and a flowrate regulator (not shown) for feeding, under pressure, the argon gas from the gas tank to the hand piece 10 at a constant flow rate. It is so arranged that argon gas flows from the gas supply unit 20 to the hand piece 10 via a flexible gas pipe 25.

The hand piece 10 internally accommodates an air-core transformer (referred to as a monostable multivibrator M below) in which 140 turns of a winding are wound on a primary side L1 and 16000 turns of a winding are wound on a secondary side L2, making the turn ratio greater than 100, and in which the primary L1 and secondary L2 are connected together and arranged in a concentric configuration. The output terminals of the secondary L2 of monostable multivibrator M are arranged so as to be freed by the connection of a needle electrode, described later, whereby a high voltage is generated to produce a unipolar discharge in the needle electrode (where the unipolar discharge refers not to a discharge generated across a pair of electrodes but a discharge into the atmosphere from an independently disposed electrode).

Figure 2:
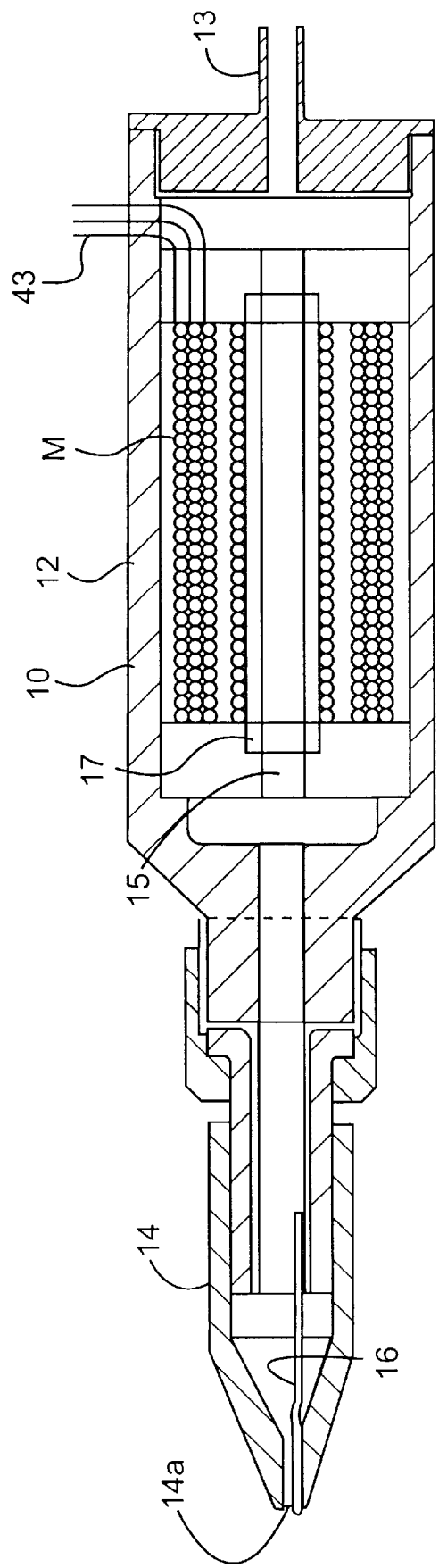
FIG. 2 is a sectional view of a hand piece of the medical coagulation apparatus according to the first embodiment.

The mechanical structure of the hand piece 10 will be described with reference to FIG. 2. The hand piece 10 has an overall length of 150 mm and is formed to a size that enables it to be grasped in such a manner that it is easy for the operator performing the surgery to handle. The hand piece 10 mainly comprises a cylindrical handle 12 for housing the monostable multivibrator M, and a nozzle 14 attached to the distal end of the handle 12. The primary and secondary windings of the monostable multivibrator M are wound concentrically on a hollow bobbin 15. A connecting portion 13 for connecting the gas pipe 25 from the above-described gas supply unit 20 is attached to the rear end of the handle 12. The argon gas supplied from the gas supply unit 20 is jetted from an opening 14a of the nozzle 14 via a gas pipe 15 communicated with the connecting portion 13. Further, a needle electrode 16 which generates an arc discharge is disposed in the opening 14a and is connected to the secondary side of the monostable multivibrator M. The primary side of the monostable multivibrator M is adapted to receive a supply of power from the power supply unit 30 via the line 43.

The operation of the medical coagulation apparatus according to the first embodiment will be described next.

First, the supply of argon gas from the gas supply unit 20 is started, then a switch SW1 on the power supply section 34 is turned on. As a result, the transformer 31 is energized, a voltage from the first smoothing circuit 32 is applied to the oscillator circuit 36, and the oscillator circuit 36 starts oscillating in accordance with the natural frequency of the crystal oscillator 35. The natural frequency is set to a frequency $[f1=1/\{2\pi(L1\cdot C1)\}]$ which causes the capacitor C1 of the amplifier section 39 and the primary side L1 of the monostable multivibrator M to oscillate.

The second smoothing circuit 33 applies a potential of +100 V to the amplifier 38 via a line 33a and a potential of −100 V via a line 33c. The amplifier 38 applies a potential of +100 V to the collector of the first transistor TR1 via a line 38a, applies a potential of −100 V to the collector side of the second transistor TR2 via a line 38c, and applies a signal from the oscillator circuit 36 to the bases of the first and second transistors TR1, TR2 via a signal line 38b. As a result, the first and second transistors TR1, TR2 are rendered conductive and non-conductive repeatedly, and current of a frequency which resonates with the primary side L1 of the monostable multivibrator M and the capacitor C1 flows into the primary side L1 of the monostable multivibrator M as described above.

The potential reaches its peak at the open end (needle electrode 16) on the secondary side of the monostable multivibrator M when current of a frequency at which the inductance on the secondary side L2 and the stray capacitance C1 on the secondary side resonate flows into the primary side L1. Since the stray capacitance Cf varies depending upon the status of the load, the resonance frequency fluctuates. In order to effect tuning to this fluctuating frequency, the automatic tuning circuit 41 sends a scanning signal to the oscillator circuit 36 via a line 36a while it monitors the potential of the secondary side L2 based upon the signal from a line 42. The oscillator circuit 36 scans the oscillating frequency over a range set based upon the scanning signal and the amplifier 38 passes a current into the primary side L1 of the monostable multivibrator M based upon this oscillating signal, whereby the potential of the secondary side L2 is made to fluctuate. When resonance is attained on the secondary side L2 and the potential is maximized, the automatic tuning circuit 41 senses this based upon the potential from the line 42 on the secondary side L2 and fixes the frequency of the oscillator circuit 36. At this time the needle electrode 16 connected to the secondary side L2 attains a potential at which it is capable of generating a unipolar discharge, and therefore an arc discharge starts being produced from the tip of the needle electrode 16.

Figure 3:
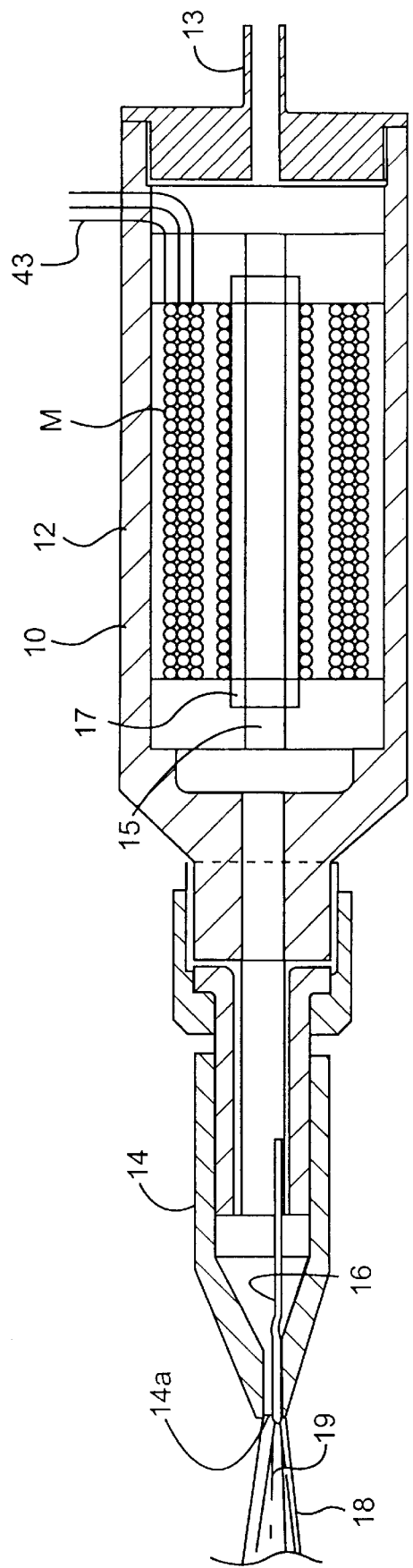
FIG. 3 is a sectional view of a hand piece of the medical coagulation apparatus according to the first embodiment.

Meanwhile, the argon gas supplied from the gas supply unit 20 is jetted from the nozzle 14 of the hand piece 10. The argon gas is ionized by the arc discharge from the needle electrode 16 and attains a plasma state. As a result, an arc discharge 19 of 5~10 mm is introduced through argon gas 18, as shown in FIG. 3.

In accordance with the first embodiment, an opposing electrode is no longer necessary because coagulation of tissue is performed by an arc produced by a unipolar discharge, and thermal burning caused by an opposing electrode can be eliminated. As a result, there is no need for a monitor circuit used heretofore to prevent thermal burning. In addition, the arc discharge from the needle electrode 16 is a unipolar discharge and accumulation of electric charge is mainly on the surface of a living body, with little current flowing into the living body, owing to the fact that the discharge from the needle electrode 16 to the tissue and the discharge from the tissue to the needle electrode 16 are merely repeated. Consequently, there is little effect upon the living body and the degree of safety is very high. Accordingly, the medical coagulation apparatus of the first embodiment can be used for surgery applied not only to organs such as the liver but also to tissue readily influence by electric current, such as the brain.

Next, a second embodiment of the invention will be described with reference to FIGS. 4 and 5. Members in the arrangement according to the second embodiment that are similar to those of the first embodiment are designated by like reference characters and a description thereof is deleted.

Figure 4:
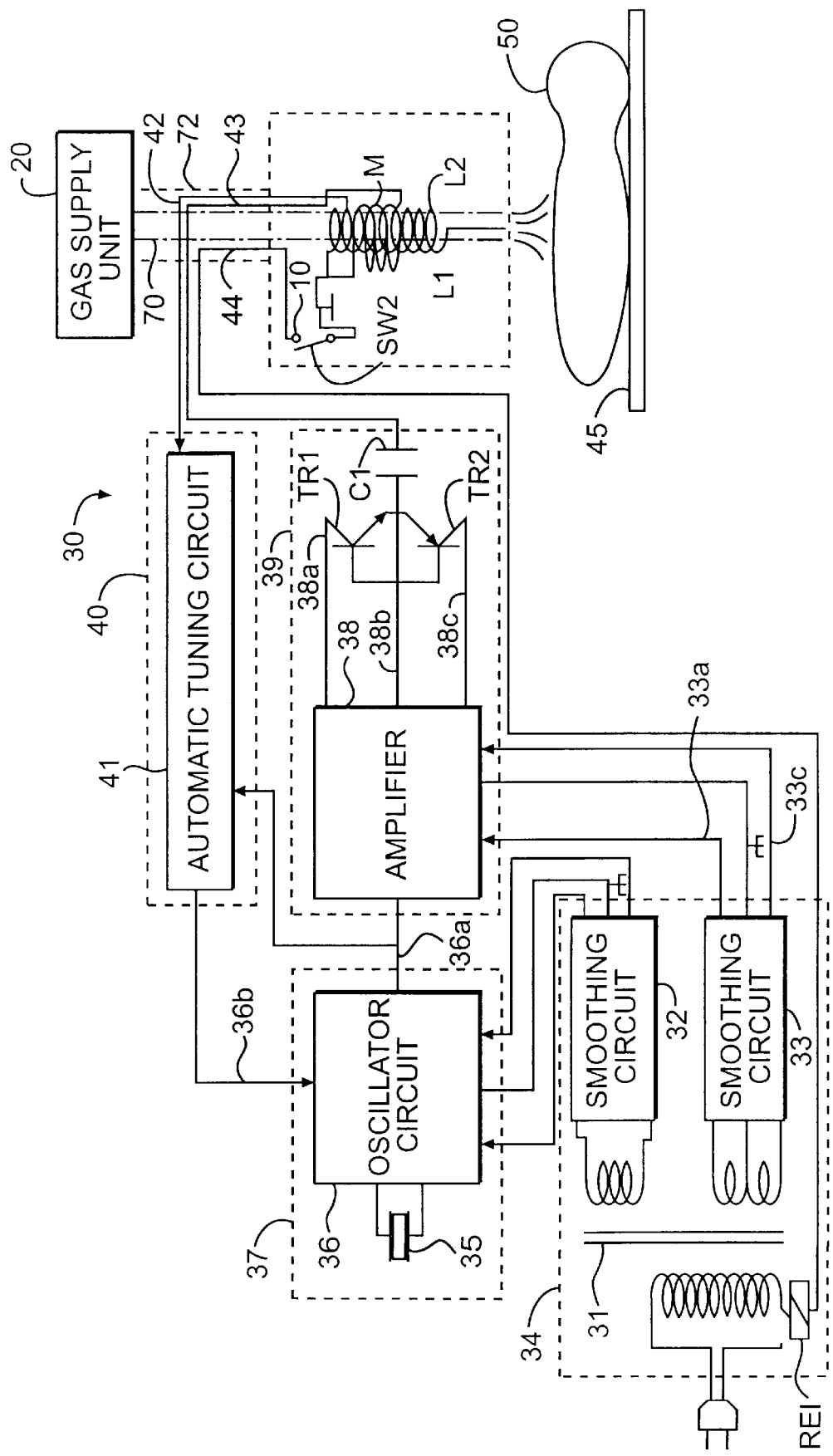
FIG. 4 is a block diagram illustrating the construction of a medical coagulation apparatus according to a second embodiment of the present invention.
Figure 5:
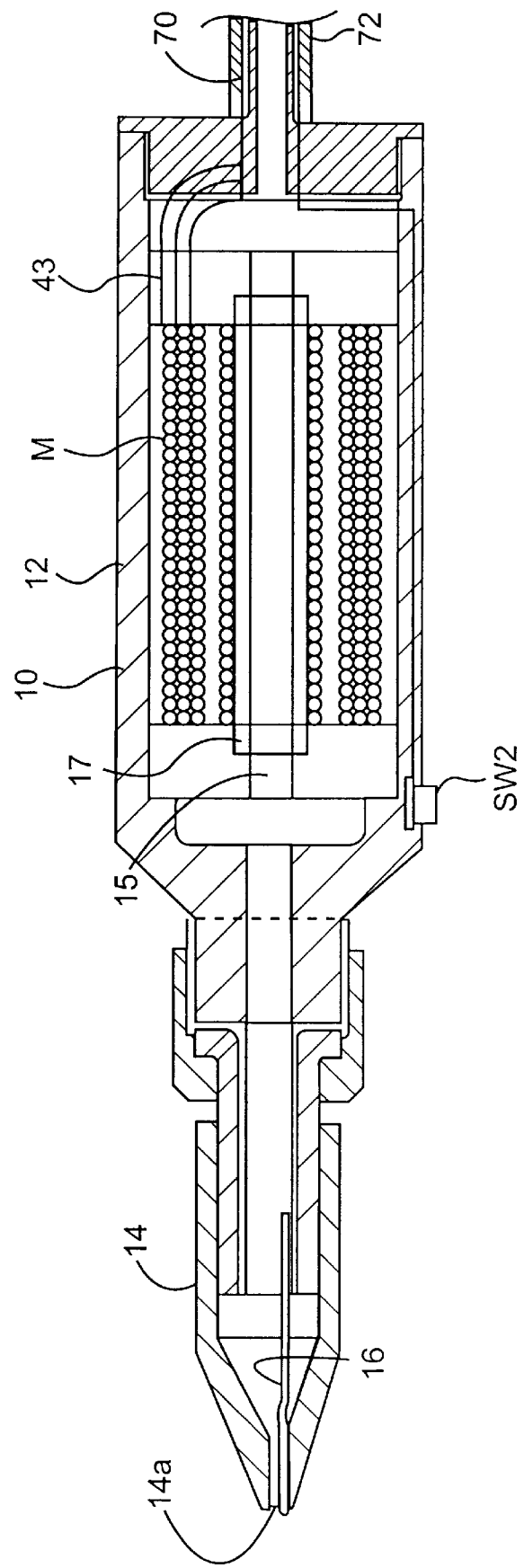
FIG. 5 is a sectional view of a hand piece of the medical coagulation apparatus according to the second embodiment.
Figure 6:
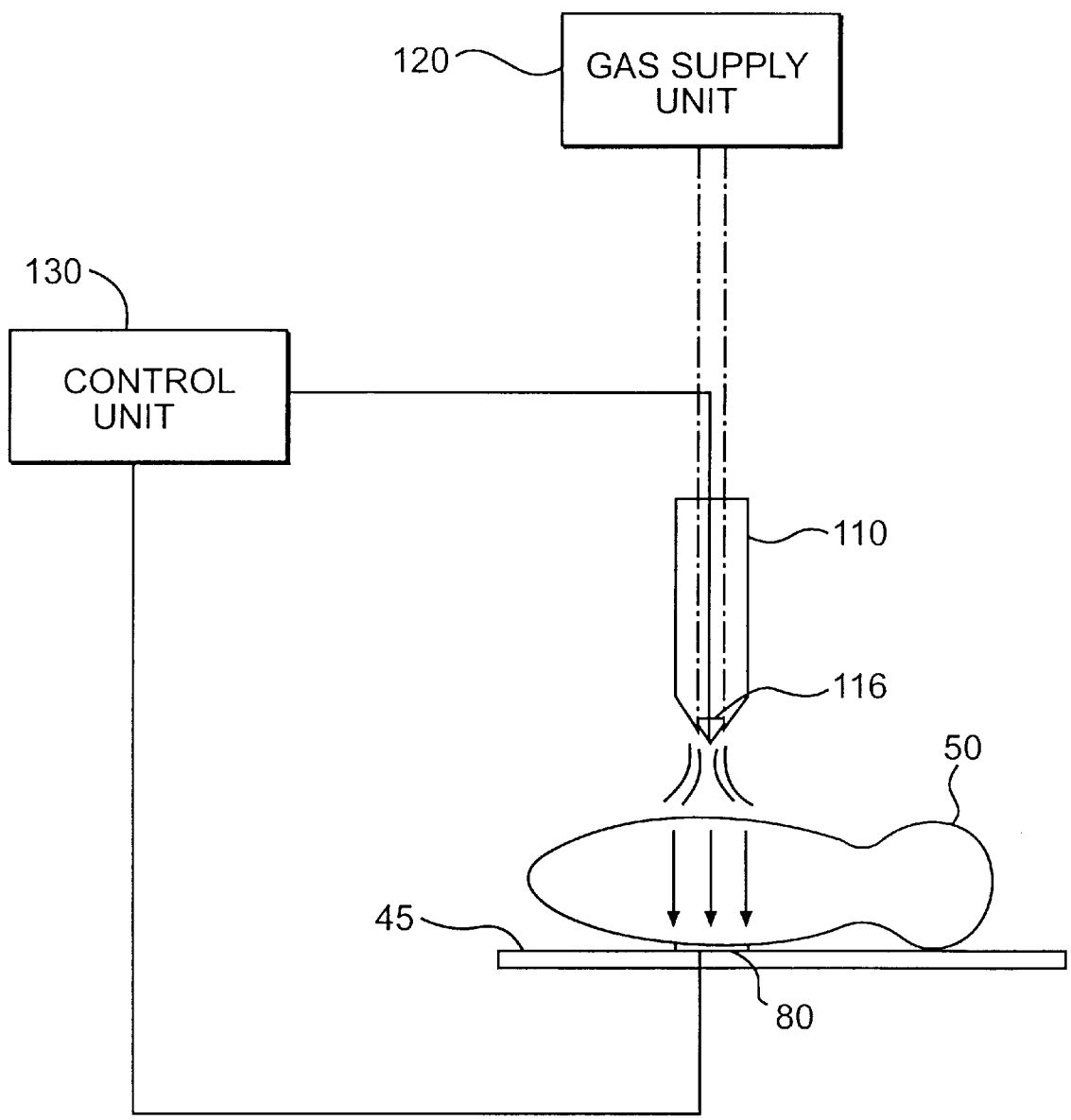
FIG. 6 is a block diagram illustrating the construction of a medical coagulation apparatus according to the prior art.

FIG. 4 shows the construction of the medical coagulation apparatus according to the second embodiment. The medical coagulation apparatus comprises the hand piece 10 for effecting coagulation and hemostasis of an affected part by irradiating the living body 50, which lies on the insulated operating table 45, with an arc discharge while a gas stream is jetted from the nozzle, the power supply unit 30 for supplying the hand piece 10 with electric power, and the gas supply unit 20 for supplying the hand piece 10 with an inert gas. It is so arranged that electric power from the power supply unit 30 and helium gas from the gas supply unit 20 are fed to the hand piece 10 via a single cable 72. Disposed in the cable 72 are a gas pipe 70 for feeding the helium gas under pressure, the line 42 by which the automatic tuning circuit 41 senses the potential on the secondary side L2 of the monostable multivibrator M, the line 43 for transmitting the power from the amplifier 39, and a control line 44 for sending the signal from a switch SW2, described later. The control line 44 is connected to a relay RE1 of the power supply section 34 and is connected also to the gas supply unit 20.

The construction of the hand piece 10 of the medical coagulation apparatus according to the second embodiment will be described next with reference to FIG. 5. The switch SW2 of push-button type is placed substantially at the central portion of the hand piece 10 and all internal wiring is connected to the single cable 72 mentioned above.

In the second embodiment, the relay RE1 of the power supply section 34 is turned on by pressing the push-button switch SW2 of the hand piece 10, as a result of which the power supply section 34 applies a voltage to the oscillator section 37 and amplifier section 39, thereby starting operation of the power supply unit 30. At the same time, the pressurized feed of helium gas from the gas supply unit 20 to the hand piece 10 starts is response to a signal from the switch SW2. Owing to the supply of power from the power supply unit 30, an arc discharge starts from the needle electrode 16 of the hand piece 10 and the supplied helium gas attains the plasma state. The helium gas in the plasma state is jetted from the nozzle 14 and the arc discharge is introduced into the plasma. Opening the switch SW2 turns off the relay RE1 of the power supply section 34. The power supply unit 30 ceases operating, the supply of helium gas from the gas supply unit 20 stops and the arc discharge from the nozzle 14 of the hand piece 10 is interrupted.

An advantage of the second embodiment is that a surgeon stanching the loss of blood at an affected part while holding the hand piece 10 is capable of freely starting and stopping the operation of the medical coagulation apparatus by pressing the push-button switch SW2 mounted on the hand piece 10.

Examples in which argon and helium are used as the inert gas have been described in the embodiments set forth above. However, as long as the gas is inert, nitrogen or the like can be used in the medical coagulation apparatus of the present invention. A gas which is readily converted to plasma by an arc discharge and forms a conductive path for the arc is best suited for actual use. Further, in the foregoing embodiments, the automatic tuning circuit 41 scans the oscillating frequency of the oscillator circuit 36 so as to produce resonance on the secondary side L2 of the monostable multivibrator M and fixing the frequency on the primary side to the resonance frequency on the secondary side by sensing the potential on the secondary side. However, it is possible to set the oscillator circuit 36 to a frequency that would produce resonance on the secondary side L2, without the automatic tuning circuit 41 being provided. Further, in the foregoing embodiments, a transformer for generating a high potential is used as the monostable multivibrator M. However, it is also possible to use a Tesla coil in stead of the transformer.

Figure 7:
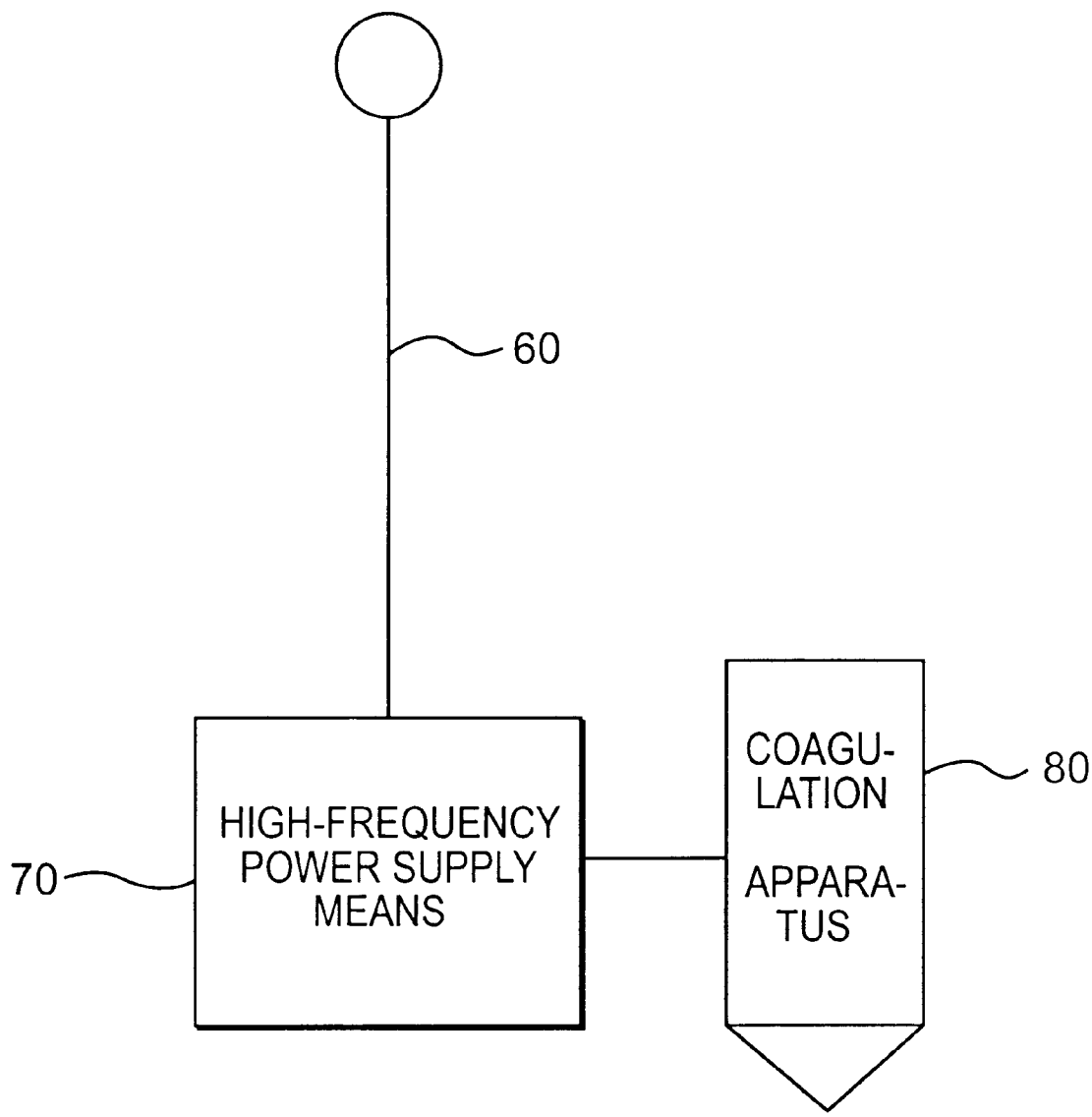
FIG. 7 is a conceptual view according to a third embodiment of the present invention.

Next, a third embodiment of the invention will be described with reference to FIG. 7. In the Figure, numeral 60 denotes an antenna, 70 high-frequency power supply means which includes the amplifier used in the first and second embodiments, and 80 a coagulation apparatus which includes a hand piece comprising the gas supply means, the monostable multivibrator and the needle electrode connected to the secondary side of the monostable multivibrator used in the first and second embodiments of the invention.

By receiving radio waves transmitted by a central hospital and supplying high-frequency current to the primary side of the monostable multivibrator, it is possible to secure means for achieving hemostasis at the time of emergency surgery at a location where a power supply is not available.

Examples of animal experiments relating to the hemostatic effect of the medical coagulation apparatus according to the arrangements of the above-described embodiments of the invention will now be set forth.

EXAMPLE 1

The abdominal region of a mouse was incised and, with the scalpel inserted into the liver, an attempt was made to stanch the flow of blood from the wound by producing a jet of plasma gas from the hand piece 10. The arc discharge induced by the plasma gas penetrated the liver tissue, the tissue protein was coagulated and desiccated and the flow of blood on the surface of the liver was stanched by the thermal energy possessed by the plasma. Since argon gas in the form of plasma is electrically conductive, a stabilized arc beam could radiate the tissue and uniform coagulation could be achieved with little energy. At this time inert argon gas jetted toward the tissue is suitably adjusted in terms of plasma temperature and the tissue is shielded from oxygen in the atmosphere. As a result, serious oxidation and carbonization of tissue is prevented. In addition, the jetted argon gas blows off blood oozing from the liver tissue and sweeps away smoke produced when the tissue is coagulated. This made it possible to visually check the portion from which the flow of blood was being stanched and to perform the blood stanching operation is reliable fashion.

EXAMPLE 2

Using a 130 g rat under ether anesthesia, three types of incisions were made in the back muscle using an electric scalpel, a laser scalpel and a plasma scalpel, and these were taken as samples.

At the same time, the surface temperature of the irradiated region was measured. When the temperature measurements of the incisions made by each of these devices were compared, a very high temperature was found at the incision made by the electric scalpel. Moreover, this temperature continued for a very long period of time. Though a hemostatic effect could be obtained, the surface of the wound was broad and severe loss of blood could not be checked.

Though the incision reached a high temperature also in the case of the laser scalpel, the temperature was much lower than in the case of electric scalpel. Moreover, loss of blood could not be stopped completely.

Though the temperature rise in the case of the plasma scalpel was small and its incising ability almost nonexistent, the plasma scalpel did exhibit a very high hemostatic ability.

It was found that these three types of incisions involved effects resulting from clearly different mechanisms. In particular, though the plasma scalpel elevated the temperature of the region being subjected to the plasma discharge, the region was cooled immediately by helium in the gas flowing together for the purpose of assisting the arc discharge. This lowered the elevation in temperature greatly.

Comparing the three types of incisions and the differences in coagulation reveals that in terms of so-called incising ability, the laser scalpel is superior owing to its precision. However, it became clear that both the laser scalpel and the electric scalpel produces a large quantity of gas. In comparison, the plasma scalpel produced almost no gas.

EXAMPLE 3

The stomach of a rabbit was cut open in an experiment, the large-sized liver was severed first by using a laser scalpel and, when extreme loss of blood occurred owing to the severing of the liver by the laser scalpel, it was determined whether the loss of blood could be stanched by a plasma scalpel. The result was that loss of blood could not be fully halted solely by the laser scalpel but that this could be achieved if a plasma scalpel were used.

Next, an experiment was conducted in which the loss of blood at the section of the liver severed by the ordinary scalpel was stanched by the plasma scalpel. As a result, it was found that a highly homogeneous carbon layer appeared at the surface. By contrast, in an experiment in which the loss of blood at the section of the liver severed by the ordinary scalpel was stanched using the laser scalpel, it was found that the laser scalpel could also stanch loss of blood if the side of the quartz and not the tip of the probe was used in making surface contact. In either method the fact that the surface of the wound reached a high temperature was confirmed by thermography, but it would found that the temperature was much lower and the evolution of gas much less with use of the plasma scalpel. On the basis of observation from the surface, it was verified that a highly uniform carbonization surface was obtained in the coagulation plane of the plasma scalpel, and it seems that this provided a significant hemostatic effect.

EXAMPLE 4

In a fourth experiment, a rabbit (having a body weight of 4.5 kg) was subjected to general anesthesia using Nembutal, the abdomen was cut open under autorespiration and the liver was exposed. The liver was incised using a laser scalpel and a plasma scalpel and each surface was observed. While the severely hemorrhaging surface at the section of the rabbit liver was pressed with a finger, an attempt was made to stop the loss of blood by both the plasma scalpel and laser scalpel. As a result, it was found that the hemostatic effect was much better in the case of the plasma scalpel. The surface was thinly and uniformly carbonized (though this evaluation must been verified later by a microscopic specimen of the tissue), and the hemostatic effect was clearly superior in the case of the plasma scalpel.

Furthermore, the liver was severed by scissors and it was attempted to stop the loss of blood at the section by the plasma scalpel. Satisfactory hemostasis could be achieved and the surface was covered with a carbonized layer. By contrast, satisfactory hemostasis could not be achieved with the laser scalpel.

EXAMPLE 5

Differences in hemostasis mechanisms were studied using tissue samples.

In a study of back muscles in an evaluated region used most commonly as the standard in a comparative study of scalpels, it was found that a thermally degenerated layer was very thick and that a thermally coagulated layer was also thick in the case of the electric scalpel. A thick carbonized layer was seen on the surface and a severe thermally burned wound surface appeared. With a laser scalpel, on the other hand, a thermally degenerated layer and a thermally coagulated layer also exist but the thickness is small and a thin carbonized layer was found on the surface. In the case of a plasma probe sample used in stanching hemorrhage after incision by a scalpel, a slight thermally degenerated layer was found but not a thermally coagulated layer. Furthermore, only a very thin carbonized layer was found to be adhering.

In a comparative study of livers, a thermally degenerated layer, a thermally coagulated layer and a blood-loss coagulation layer were found to be very thick at a tissue section incised and coagulated by a laser scalpel, and a thinly carbonized layer was found on the surface. Samples in which there was residual loss of blood under the carbonized layer also existed. In samples that were coagulated by a plasma scalpel after being incised by the laser scalpel, the thermally degenerated layer and thermally coagulated layer were substantially equivalent to those produced when an incision was made by the laser scalpel, and it was found that the coagulated layer of blood had a thinly carbonized layer on its surface.

Industrial Applicability

Unlike the conventional mechanism in which an electric scalpel having a spray coagulation function or an argon beam coagulator passes a high-frequency current into a living body using plasma as the conductor and coagulates and stanches the flow of blood by Joule heating, the medical coagulation apparatus based upon claims 1–4 of the invention of this application does not place an opposing electrode on the living body and, hence, does not pass a high-frequency current into the body. The mechanism of coagulation and hemostasis of blood is based upon the local energy possessed by a plasma flow. As a result, thermal burning and tissue damage that can affect the nervous system, which are caused by the high-frequency current constituting the problem of the prior art, do not occur and it is possible to readily perform surgery on a patient requiring rest.

Further, even in case of emergency surgery on a seriously ill patient who should not be moved from the particular location, it is possible to achieve hemostasis at the time of on-site surgery by receiving radio waves transmitted to the location from a central hospital. As set forth above, the coagulation apparatus of the present invention excels in protecting the safety of the living body and, at the same time, makes it possible to perform surgery on a patient for which a stress load is not allowed. Thus, the coagulation apparatus of the invention fills needs in the medical industry that could not be met with the prior art.

What is claimed is:

1. A medical coagulation apparatus comprising:

inert gas supply means for supplying an inert gas;

a casing formed to have a size capable of being grasped and having a jet nozzle for guiding the inert gas supplied from said inert gas supply means;

a transformer housed within said casing and having a winding of a small number of turns wound on a primary side and a winding of a large number of turns wound on a secondary side, one end of the secondary side floating or being connected to the primary side and the other end being connected to a discharge portion placed in the proximity of the jet nozzle of said casing; and power supply means connected to the primary side of said transformer for producing a single-pole discharge at the discharge portion connected to the secondary side of the transformer, accumulating electric charge on the surface of a living body by electrostatic induction between the apparatus and the living body, and passing a current, which has a frequency that generates a high potential for supplying electrical energy, into the primary side.

2. A medical coagulation apparatus according to claim 1, wherein said power supply means passes a current, which has a frequency that causes resonance on the secondary side of the transformer, into the primary side.

3. A medical coagulation apparatus comprising:

inert gas supply means for supplying an inert gas;

a casing formed to have a size capable of being grasped and having a jet nozzle for guiding the inert gas supplied from said inert gas supply means;

a transformer housed within said casing and having a winding of a small number of turns wound on a primary side and a winding of a large number of turns wound on a secondary side, the primary side floating, one end of the second side floating or being connected to the primary side and the other end being connected to a discharge portion placed in the proximity of the jet nozzle of said casing;

power supply means connected to the other end of the primary side of said transformer for passing a current of a regulated frequency into said primary side; and frequency regulating means for regulating frequency of said power supply means to a frequency that generates a high potential for producing a single-pole discharge in the discharge portion connected to the secondary side of the transformer.

4. A medical coagulation apparatus according to claim 3, wherein said frequency regulating means regulates the frequency of said power supply means to a frequency that causes resonance on the secondary side of the transformer.

5. A medical coagulation apparatus comprising:

inert gas supply means for supplying an inert gas;

a casing formed to have a size capable of being grasped and having a jet nozzle for guiding the inert gas supplied from said inert gas supply means, and a needle electrode placed in the proximity of said jet nozzle;

a transformer housed within said casing and having a winding of a small number of turns wound on a primary side and a winding of a large number of turns wound on a secondary side, one end of the secondary side floating or being connected to the primary side and the other end being connected to a discharge portion placed in the proximity of the jet nozzle of said casing; and power supply means connected to the primary side of said transformer for producing a plasma of an inert gas, which is supplied from the inert gas supply means, by a unipolar discharge at the discharge portion connected to the secondary side of the transformer, accumulating electric charge on the surface of a living body by electrostatic induction between the apparatus and the living body, and passing a current, which has a frequency that generates a high potential for supplying electrical energy, into the primary side.

6. A medical coagulation apparatus according to claim 5, wherein said power supply means passes a current, which has a frequency that causes resonance on the secondary side of the transformer, into the primary side.

7. A medical coagulation apparatus comprising:

inert gas supply means for supplying an inert gas;

a casing formed to have a size capable of being grasped and having a jet nozzle for guiding the inert gas supplied from said inert gas supplying means, and a needle electrode placed in the proximity of said jet nozzle;

a transformer housed within said casing and having a winding of a small number of turns wound on a primary side and a winding of a large number of turns wound on a connected to the primary side and the other end being connected to a discharge portion placed in the proximity of the jet nozzle of said casing;

power supply means connected to the other end of the primary side of said transformer for passing a current of a regulated frequency into said primary side; and frequency regulating means for regulating frequency of said power supply means to a frequency that generates a high potential for producing a single-pole discharge in the discharge portion connected to the secondary side of the transformer.

8. A medical coagulation apparatus according to claim 7, wherein said frequency regulating means regulates the frequency of said power supply means to a frequency that causes resonance on the secondary side of the transformer.

\* \* \* \* \*

UNITED STATES PATENT AND TRADEMARK OFFICE
CERTIFICATE OF CORRECTION

PATENT NO. : 6,013,075
DATED : January 11, 2000
INVENTOR(S) : Stanislav AVRAMENKO et al.

It is certified that error appears in the above-identified patent and that said Letters Patent is hereby corrected as shown below:

Claim 7, Column 10, line 62, before connected", insert --secondary side--, the primary side floating, one end of the second side floating or being--.

Signed and Sealed this

Nineteenth Day of December, 2000

Attest:

Q. TODD DICKINSON

*Attesting Officer*      *Commissioner of Patents and Trademarks*